United States Patent [19]
Patchornik et al.

[11] 4,037,037
[45] July 19, 1977

[54] NOVEL METHOD OF ORGANIC SYNTHESIS TO FORM A POLYMER-BOUND ACTIVE SPECIES

[75] Inventors: Avraham Patchornik, Ness-Ziona; Menahem A. Kraus, Rehovot, both of Israel

[73] Assignee: Yeda Research & Development Co. Ltd., Rehovot, Israel

[21] Appl. No.: 498,583

[22] Filed: Aug. 19, 1974

Related U.S. Application Data

[63] Continuation-in-part of Ser. No. 167,022, July 28, 1971, abandoned.

[51] Int. Cl.$^2$ .................. C08C 19/12; C08F 8/18; C08C 19/00; C08F 210/00
[52] U.S. Cl. .................. 526/46; 260/586 R; 260/590 E; 260/592; 526/19; 526/21; 526/47
[58] Field of Search ........... 260/590, 88.2 C, 88.2 S, 260/93.5 A, 89.7 S; 526/19, 21, 46, 47, 30

[56]  References Cited
U.S. PATENT DOCUMENTS

| | | | |
|---|---|---|---|
| 3,008,927 | 11/1961 | Seifert | 260/88.2 S |
| 3,297,648 | 1/1967 | Corte et al. | 260/88.2 S |
| 3,625,870 | 12/1971 | Norwood | 260/88.2 S |

OTHER PUBLICATIONS

Organic RXS, vol. 15, "Dieckmann Condensations", John P. Schaefer et al., (pp. 40–46 in particular) QD 25107, Editor Adams et al., R. B. Merrifield, July 20, 1963, JACS, pp. 2149-2154, vol. 85.

*Primary Examiner*—Joseph L. Schofer
*Assistant Examiner*—Herbert J. Lilling
*Attorney, Agent, or Firm*—Ostrolenk, Faber, Gerb & Soffen

[57]  ABSTRACT

The present invention relates to a novel process of organic synthesis which comprises forming active species from molecules chemically bound to a rigid insoluble polymer, reacting the active species so as to obtain the desired product, splitting this off the polymer, and recovering the desired product. The novel method of organic synthesis is applicable to a wide variety of chemical reactions, and the conditions of reaction will be chosen according to the desired products.

3 Claims, No Drawings

NOVEL METHOD OF ORGANIC SYNTHESIS TO FORM A POLYMER-BOUND ACTIVE SPECIES

This is a continuation-in-part of application Ser. No. 167,022 filed July 28, 1971 and now abandoned.

BACKGROUND OF THE INVENTION

Hitherto extensive use has been made of polymers in the synthesis of linear peptides and oligonucleotides. The advantage of these methods is that high yields can be obtained in each step of the synthesis by using a large excess of either soluble or insoluble reagent. The desired products can be easily separated from excess of reactants by filtration of the resin.

The alpha-alkylation of carboxylic esters having more than one alpha-hydrogen is accompanied generally by an extensive ester condensation, and to varying degrees by dialkylation. Some solutions have been offered, such as the use of t-butyl esters with lithium amide as base in liquid ammonia. It has also been shown that metalated carboxylic acids and 2-oxazoline derivatives of acids undergo alkylation without condensation.

In conventional acylations of esters having more than one alpha-hydrogen with acyl halides or anhydrides, at least two competing reactions take place resulting in the formation of the self-condensation product of the ester and the diacylated ester. Such competing reactions are undesired as a mixture of products is obtained. It is possible to carry out the reaction in very dilute solutions, but this too is inconvenient and expensive.

SUMMARY OF THE INVENTION

The present invention relates to a novel process of organic synthesis, to novel means for effecting such process and to the products obtained by the novel process. Other and further aspects of the present invention will become apparent hereinafter.

According to the present invention reactive species are formed on a rigid, insoluble polymer, reacted, and the resulting product is split off from the polymer and recovered.

According to one embodiment of the invention reactive species are formed on a cross-linked, rigid, insoluble polymer, the concentration of the bound reactive species being such as to prevent the mutual interaction of same. Due to the cross-linking of the polymer, the free motion of the carrier-bound reactive species is greatly restricted. Under these conditions, the reaction of the bound reactive species with a soluble reagent takes place as if the reaction would be effected in a very dilute solution, yet the concentration of the bound species and the conversion of the reactants can be quite high.

This reaction can be depicted schematically as follows:

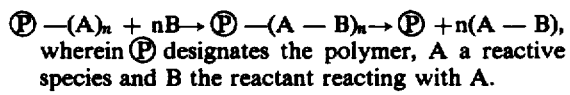

wherein Ⓟ designates the polymer, A a reactive species and B the reactant reacting with A.

It is also possible to effect an intramolecular reaction, such as cyclization, making use of the carrier-bound reactive species according to the scheme

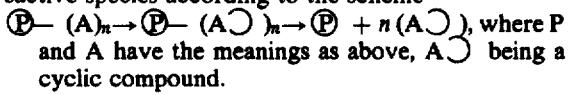, where P and A have the meanings as above, A⟲ being a cyclic compound.

It is clear that the product A-B or the cyclic product A⟲ can be separated from the carrier.

According to a preferred embodiment of the invention, a suitable polymer, such as polystyrene-divinylbenzene copolymer is chloromethylated, the chloromethylated polymer is reacted with a carboyxlic acid, then with trityllithium and with either an alkyl halide to obtain as product an alkylated acid or with an acyl halide to obtain an acylated product, and the desired product is split off from the polymer by suitable means, such as hydrogen bormide in trifluoroacetic acid.

According to a further embodiment, two different species are chemically linked to a rigid cross-linked insoluble polymer, one at a higher, the other at a lower concentration, and these are reacted so as to form the desired product. According to this embodiment it is possible, for example, to produce beta-ketoacids and ketones. For example, a polymer is chloromethylated, reacted with a small quantity of an enolizable acid, subsequently with an excess of a non-enolizable acid, then with trityllithium and after the interaction of the two carrier-bound species, the resulting beta-ketoacid is split off, and if desired, converted by decarboxylation to a ketone.

According to the first embodiment, the active species behaves as if in an infinitely dilute solution, without side-reactions. According to the second embodiment, reaction takes place between the two bound species due to the proximity of these, imposed by the rigid polymer.

The above novel method of organic synthesis is applicable to a wide variety of chemical reactions, and the conditions of reaction will be chosen according to the desired products.

DESCRIPTION OF THE PREFERRED EMBODIMENT

In the following, the invention is illustrated with reference to the acylation of polymer-bound ester enolates. It is clear that this is by way of example only and that a wide spectrum of organic reactions can be effected with the aid of the novel carrier-bound reactive species, which can be of any desired type.

The drawbacks of conventional methods are obviated by the process of the present invention and practically only the desired product is obtained, the concentrations being quite high.

The carboxylic acid to be acylated is first bound to an insoluble cross-linked polymer, resulting in an ester

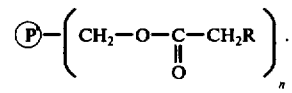

As long as the distance between the reactive species is adequate, practically no side-reactions will take place. By adding a suitable base, polymer bound enolate ions are formed, and as these are separated from other such ions and from un-ionized ester groups, they can react only with the added acyl halide, resulting in the desired product only.

Esters of phenylacetic acid and of acetic acid were acylated. These were obtained by reacting the corresponding acid with chloromethylated polystyrene-2% divinylbenzene, 4-6% Cl, in the presence of an equivalent amount of triethylamine. The product contained 0.1 to 0.3 millimoles of ester per gram of polymer. The remaining chloromethyl groups were destroyed by adding ethyl mercaptan. The polymer-bound ester was swelled in toluene/20% - 1,2-dimethoxyethane; an equivalent amount of trityllithium in tetrahydrofuran was added at 0° C. under dry argon. After the disappearance of the red color of the base, 1.5 equivalents of acid chloride or anhydride were added and the reaction mixture was stirred at ambient temperature during 1 hour. The polymer was filtered, washed with benzene, chloroform, ethanol, water and methanol and dried in a vacuum oven. The product and unreacted acid were cleaved from the polymer by dry hydrogen bromide in trifluoroacetic acid at ambient temperature (3 hours). Only a single ketone and unreacted acid were obtained in all cases.

The reaction sequence can be shown schematically as follows:

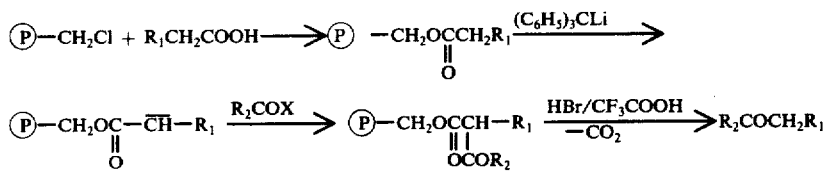

wherein X designates —Cl or —OCR$_2$.
                            ‖
                            O In all the runs, the ketone was separated from the unreacted acid by chromatography and identified by NMR, IR and mass-spectra. The results are summarized in the following Table I.

Taking into account the unreacted acid, yields of ketones are quite high (70–90%).

reacting chloromethylated polystyrene-2%-divinylbenzene with an excess of the monosodium salts of alpha, omega-diols. The compound derived from ethylene glycol, (P)—CH$_2$—OCH$_2$CH$_2$OH, (1 mmole/g) showed mainly free OH absorption (3580cm$^{-1}$, sharp) while the corresponding 1,4- butane diol derivative (P)—CH$_2$-—O—(CH$_2$)$_4$OH (1 mmole/g) showed a weak free OH band and a much stronger hydrogen-bonded absorption (3300cm$^{-1}$, broad).

The same technique was used also for carrying out cyclization reactions of polymer-bound molecules. Good yields of pure carbocyclic compounds having 5 and 6-membered rings were obtained. There was carried out the reaction of alpha, omega-dibromoalkanes with polymer-bound malonate,

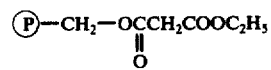

and the Dieckmann cyclization [see Schafer et al, Or-

TABLE I

| ESTER | ACYLATING AGENT | PRODUCT | M.P. °C (lit) | YIELD |
|---|---|---|---|---|
| (P)—CH$_2$—OCCH$_2$C$_6$H$_5$ ‖ O | NO$_2$—⟨⟩—COCl | NO$_2$—⟨⟩—COCH$_2$—⟨⟩ | 159–160 (156-7) | 43% |
| (P)—CH$_2$—OCCH$_2$C$_6$H$_5$ ‖ O | Br—⟨⟩—COCl | Br—⟨⟩—COCH$_2$—⟨⟩ | 104–6 (103) | 40% |
| (P)—CH$_2$—OCCH$_2$C$_6$H$_5$ ‖ O | [⟨⟩—CH$_2$CO]$_2$—O | ⟨⟩—CH$_2$COCH$_2$—⟨⟩ | 57–58 (58.5) | 40% |
| (P)—CH$_2$—OCCH$_3$ ‖ O | NO$_2$—⟨⟩—COCl | NO$_2$—⟨⟩—COCH$_3$ | 80–81 (79-80) | 20% |

In the above examples 40–55% unreacted acid were revovered.

The results were compared with analogous reactions in solution. Ethyl phenylacetate was added to trityllithium solution until the red color disappeared. After addition of 1.5 equivalents of p-nitrobenzoyl chloride the mixture was stirred for 1 hour. Acid hydrolysis of the crude product resulted in a mixture containing five 2,4-dinitrophenylhydrazine-(DNP) -positive compounds. The yield of 4'-nitro-2-phenyl acetophenone was 22%.

Spectroscopic evidence was obtained for the polymeric dilution effect due to the binding of the reactive species to the polymeric carrier. This was shown with carrier-bound species of the type (P)—CH$_2$—O(CH$_2$)$_n$-—OH. Such carrier-bound alcohols were obtained by ganic Reactions, 15, 1 (1967)] of diesters of the type

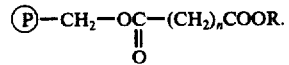

When n was 8 and 14 in the case of the Dieckmann cyclization, 9- and 15-membered rings were formed.

In a similar manner, esters can be alkylated. According to this embodiment of the invention, there is provided a method for the alkylation of esters which comprises covalently binding ester enolate ions to a polymer network, alkylating the enolate and cleaving the product from the polymer carrier.

The immobilization on the polymer prevents the interaction of the ester enolate ions, and thus there is no condensation or proton exchange between these species. This is mainly due to the rigid polymer-structure to which the enolate species are bound. As a result of the cleavage, there are obtained only monoalkylated acids.

The novel method comprises chloromethylating commercial polystyrene-2%-divinylbenzene to provide a polymer containing 3-5% chlorine. The carboxylic acid which is to be alkylated is bound to the chloromethylated polymer, so as to obtain a content of from 0.1 to 0.2 millimoles of ester per gram of polymer. The remaining chloromethyl groups are removed by reaction with ethyl mercaptan in dimethylformamide or by similar means, the dry polymer ester is reacted with tritylithium and an alkyl halide and the product is cleaved by means of hydrogen bromide in trifluoroacetic acid or by similar means.

The reaction is illustrated by the following reaction scheme:

rier was effected by means of HBr in trifluoroacetic acid at room temperature (2hours). Quantitative cleavage was indicated by the complete disappearance of the ester carbonyl absorption in the IR spectrum of the polymer. In every experiment, a single alkylation product was obtained (thin layer chromatography [TLC] and no self-condensation was observed. The product was purified by preparative TLC and identified by IR, NMR and mass spectra.

The results are summarized in Table II.

TABLE II

| | The Alkylation of Polymer-Esters | | |
|---|---|---|---|
| Ester | Alkylating Agent | Product | Yield$^a$ % |
| ⓟ—CH$_2$OCCH$_2$C$_6$H$_5$ ‖ O | CH$_3$I | C$_6$H$_5$CH—COOH \| CH$_3$ | 85 |
| ⓟ—CH$_2$OCCH$_2$C$_6$H$_5$ ‖ O | C$_6$H$_5$CH$_2$Br | C$_6$H$_5$CH—COOH \| CH$_2$C$_6$H$_5$ | 50 |
| ⓟ—CH$_2$OC(CH$_2$)$_2$C$_6$H$_5$ ‖ O | n-C$_4$H$_9$I | C$_6$H$_5$CH$_2$CH—COOH \| C$_4$H$_9$ | 45 |

$^a$Based on the amount of purified product relative to that of starting ester.

The process set out above is of general applicability and may be used with other enolates than those derived from esters.

According to a further embodiment of the invention, two different compounds are bound chemically to the same polymer, one at low concentration and the other at high concentration, resulting in a close proximity of the molecules which are intended to react with each other, and after their interaction the desired product is split off and recovered. This reaction is the other extreme of the polymeric immobilizing effect. This "intrapolymeric" reaction is characterized by a high de-

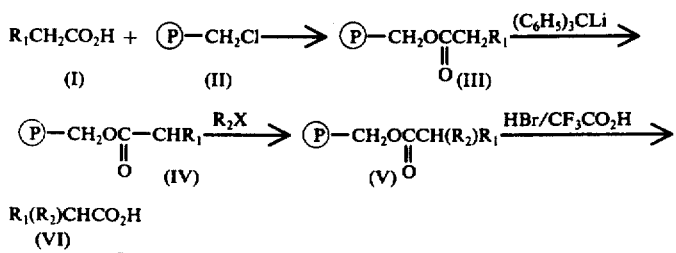

wherein ⓟ designates the insoluble polymer and wherein X designates halogen.

The dry polymer ester (III) was suspended in toluene - 20% 1,2-dimethoxyethane and a equivalent amount of a 0.5 N solution of trityllithium in tetrahydrofuran was added under argon at room temperature. After the disappearance of the red color (a few minutes), 1.5 equivalents of an alkyl halide were added and the mixture stirred for 15 minutes. The polymer (V) was then filtered and washed successively with ethanol, water, dioxane, water, methanol, benzene and methanol. Cleavage of the product (VI) from the polymeric cargree of selectivity and high yields. The reaction is illustrated with reference to the mixed ester condensation of two acids bound to a common polymer backbone. A small quantity of an enolizable acid is bound to a chloromethylated polymer, such as polystyrene-divinylbenzene by Merrifield's method (see J.Am.Chem. Soc. 85, 2149), the resulting polymer is reacted with an excess of a non-enolizable acid, and after the reaction of the two species, the desired product, a beta-ketoacid is split off, and if desired, converted to a ketone.

The reaction is illustrated in the following scheme:

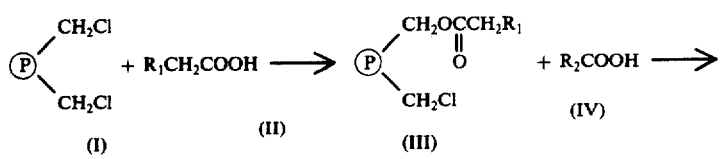

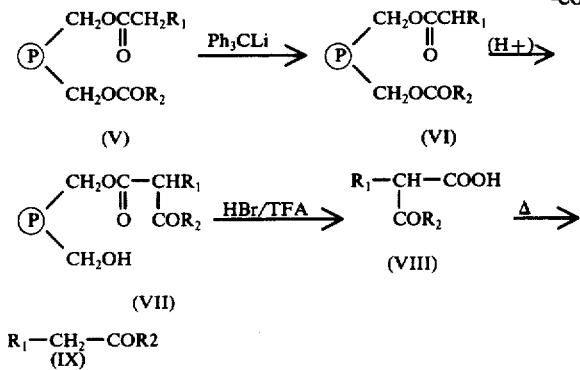

(VII)

R₁—CH₂—COR2
(IX)

An enolizable acid (II) was bound to chloromethylated polystyrene-2% divinylbenzene by the Merrifield's method. Ethyl diisopropyl amine was used instead of triethylamine. The final concentration of the ester moieties of (II) in the product (III) was kept low, (see the following Table) by limiting either the amount of the acid (II) or the duration of the reaction.

The polymer was filtered and washed successively with ethanol, water, dioxane, water, ethanol, benzene and methanol and dried in a vacuum oven at 60° C. Polymer (III) was then treated with an excess of a second, non-enolizable acid (IV). The concentration of the ester moieties of (IV) in the product (V) was 0.6–1.7 mmole/gr, depending on the original chlorine content of the polymer. After washing and drying as before, the polymer was suspended in dry toluene - 1,2-dimethoxyethane (DME) under argon, and a solution of trityllithium in THF or in DME was added at room temperature. The amount of base added was equivalent to that of moieties of acid (II) in polymer (V). The red color of the base disappeared within two or three minutes. After stirring the suspension for a further five minutes, it was neutralized with acetic acid, and the polymer was filtered and washed thoroughly as described above. Cleavage of the product and unreacted acid from the polymer was effected by dry HBr in trifluoroacetic acid (TFA) (2 hours at room temperature). The polymer was filtered and washed thoroughly with benzene, ether and chloroform. These solvents were replaced by toluene and the solution was refluxed for half an hour to effect decarboxylation of the beta-ketoacid (VIII). The resulting solution contained a single ketone (IX) in every case. The mixture obtained by the above procedure was remarkably uncomplicated, the only major by-product being unreacted acid (IV) and (II) (thin layer chromatography [TLC]). The ketone could thus be isolated simply by extracting the solution with dilute carbonate. For purposes of analysis, the ketones were further purified by preparative TLC. They were identified by their melting points and by NMR, IR and mass spectra. Results are summarized in Table III.

It will be noted that the yield of ketone (IX) increases with increasing ratio of non-enolizable to enolizable ester in polymer (V). Apparently at sufficiently high ratios and absolute concentrations, the majority of enolizable ester groups have some non-enolizable ester moieties in their vicinity, hence the high yields.

These results were compared with analogous reactions in solution in which mixtures of an enolizable and a non- enolizable benzyl ester were treated with trityllithium. Concentrations, mole ratio, temperature and reaction times were identical to those used in the analogous reaction on the polymer.

In all such experiments, the results were poorer than those on the polymer. Yields were generally lower (see Table) and the mixtures obtained upon hydrolysis (HBr in TFA) and decarboxylation were of much greater complexity, consisting of at least six major components (TLC). High ratios of non-enolizable to enolizable ester.

In order to confirm the mechanism proposed in scheme 1, equal amounts of two different batches of polymer, each containing a different ester were mixed and treated with tritylllithium for ten minutes. One batch contained p-chlorobenzoate groups (1 mmole/g). The other 3-phenylpropionate (0.1 mmole/g). Upon cleavage and work-up as described above, no ketones whatsoever could be detected (TLC), the only products being unreacted starting acids. This result indicates that the condensations described are truly intrapolymeric and no mechanism such as cleavage followed by condensation is involved.

TABLE III

The Condensation of Two Esters Bound to a Common Polymer Backbone

| Enolizable acid (II) | Concentration of ester of II in polymer V mmole/g | Non-enolizable acid (IV) | Concentration of ester of (IV) in polymer (V) mmole/g | Product | Yield % | Yield of analogous reaction in solution |
|---|---|---|---|---|---|---|
| $CH_3(CH_2)_6CO_2H$ | 0.20 | p-$ClC_6H_4CO_2H$ | 0.60 | p-$ClC_6H_4CO(CH_2)_6CH3$ | 35 | 30 |
| $C_6H_5CH_2CO_2H$ | 0.11 | $C_6H_5CO_2H$ | 0.52 | $C_6H_5COCH_2C_6H5$ | 45 | — |
| $C_6H_5(CH_2)_2CO_2H$ | 0.10 | $C_6H_5CO_2H$ | 1.01 | $C_6H_5CO(CH_2)_2C_6H5$ | 85 | 42 |
| $CH_3(CH_2)_4CO_2H$ | 0.07 | $C_6H_5CO_2H$ | 1.71 | $C_6H_5CO(CH_2)_4CH3$ | 95 | — |
| $C_6H_5(CH_2)_2CO_2H$ | 0.04 | p-$ClC_6H_4CO_2H$ | 1.70 | p-$ClC_6H_4CO(CH_2)_2C_6H5$ | 85 | 20 |

Although the present invention has been described above with particular reference to specific embodiments, the invention is not so limited. It will be recognized that the progress described involves the formation of a stable and isolated carbanion, i.e., enolate, which can then be used in a great variety of reactions including, without limitation, alkylation, acylation, cyclization, and many other chemical reactions. The stable and isolated enolate is obtained by covalently bonding a suitable enolizable compound to a rigid insoluble cross-linked polymer through linking groups which are also covalently bound to the polymer. The resulting enolizable compound bound polymer is then reacted with a suitable enolizing agent in the presence of an inert solvent to convert the enolizable compound to the stable and isolated enolate.

Although the specific embodiments described hereinbefore have utilized polystyrene-divinylbenzene as the isoluble polymer, many other suitable polymers could be used. Other insoluble polymers include polyphenyls, polyvinyl naphthalene, aromatic polyamides, polystyrene, synthetic polyamino acids, synthetic polyacrylamide gels, aromatic polyimides, and the like. The particular identity of the polymer is of secondary importance so long as it is rigid, insoluble, and inert to the reactions occurring, since the polymer is merely a carrier for the enolate.

Similarly, the present invention is not restricted to the use of chloromethylene groups as the covalent linking groups. Other di-functional linking groups such as —NH—, —S—, —COO—, and the like can be used. In like manner, the covalent linking of the linking group to the polymer is not restricted to chloromethylation as described in the foregoing specific embodments. Other methods will be apparent to the skilled chemist as, for example, the preparation of a hydroxymethylated polymer by acetylation of the polymer, oxidation to an acid followed by reduction to the hydroxymethyl group.

In the foregoing specific embodiments, the enolizing agent employed was trityllithium and the inert solvent was either tetrahydrofuran or dimethoxyethane. Here also, the invention is not limited to these particular materials. Other enolizing agents such as lithium diisopropylamide, lithium isopropyl cyclohexylamide, lithium-2,2,6,6-tetramethyl piperidide, sodium tert. amylate, etc. and other inert solvents such as dioxane, N,N-dimethylformamide, dimethylsulfoxide, hexamethyl phosphoramide, etc. can also be employed. Similarly, HBr was used in the above examples to split the product from the polymer and other splitting agents can be used such as NaOH, sodium ethoxide methanolic diazomethane, etc.

The formation of the enolizable compound bound polymer in the process of this invention bears a great deal of similarity to the preparation of an affinity chromatography reagent. The major differences are that the material linked to the carrier in this process must be an enolizable compound and that hydrophilic polymers are preferably used in affinity chromatography whereas the polymers employed as carriers in this invention are preferably lyophilic. Of course, what is done with the compound bound polymer in this invention and in affinity chromatography are quite different.

As examples of other embodiments of the present invention, the following Examples are set forth.

EXAMPLE 1

3-phenylpropanoic acid is attached to chloromethylated "popcorn" polystyrene (0.15 mmol/gr). Excess chloromethyl groups are treated with ethyl mercaptan. The ester enolate is formed by treating the polymerester with an equivalent amount of lithium diisopropylamide in tetrahydrofurane at room temperature. The enolate is reacted with gaseous carbon dioxide. The carboxylated ester is cleaved from the polymer by methanolic diazomethane. Dimethyl bentyl malonate is obtained in 52% yield.

EXAMPLE 2

Octanoic acid is attached to chloromethylated macroporous (30% cross linked) polystyrene (0.13 mmol/gr). The ester enolate is formed by treating the polymerester with lithium 2,2,6,6-tetramethyl piperidide in tetrahydrofurane-hexamethylphosphoramide. The enolate is reacted with ethyl chloroformate. The product is cleaved off from the polymer by treatment with sodium ethoxide at room temperature. The desired product, diethyl-n-hexyl malonate is obtained in 45% yield.

EXAMPLE 3

Ethyl malonate half ester was attached to chloromethylated popcorn polystyrene (0.10 mmol/gr). The polymer malonate ester obtained was treated with an equivalent amount of 1.5 dibromopentane and 2 equivalents of sodium tert. amylate in toluene. The product 1-carboethoxycyclohexane carboxylic acid was obtained in 85% yield.

EXAMPLE 4

2-(1,3-dihydroxypropyl) polystyrene was obtained by treating chloromethyl macroporous polystyrene with sodium diethyl malonate and reduction of the product with lithium aluminum hydride. 1.4-cyclohexanedione was attached as monoketal to the dihydroxypropyl polymer by refluxing in benzene in the presence of toluenesulfonic acid. The ketone enolate was obtained by treating the resulting polymer with an equivalent of trityllithium. The enolate was alkylated by methyl iodide. The product, 2-methyl-1,4-cyclohexanedione was obtained by cleavage with acetone containing $H_2So_4$.

EXAMPLE 5

As example 1, wherein the polymeric carrier is polyvinyl naphthalene.

Various changes and modifications can be made in the process of the instant invention without departing from the spirit and scope thereof. For example, it will be recognized that the particular polymer, linking agent, enolizable compound and enolizing agent are not of great importance when each is considered individually and a multitude of materials can be employed as long as they satisfy the general requirements for each of these agents. The various embodiments set forth herein were for the purpose of further illustrating the invention but were not intended to limit it.

We claim:

1. A method of forming a stable enolate in an inert solvent which comprises covalently bonding a plurality of linking groups to an insoluble cross-linked polymer, covalently bonding an enolizable compound to at least one of said linking groups so as to provide at least one side chain of the enolizable compound covalently bound to the polymer network, and reacting the enolizable compound bound polymer with an enolizing agent in the presence of an inert solvent to provide at least one enolate covalently bound to the polymer network.

2. The method of claim 1 wherein a plurality of enolates are covalently bound to the polymer network at a distance from one another so as to prevent their interaction.

3. The method of claim 1 wherein at least one nonenolizable compound is covalently bound to at least one of said linking groups whereby a reaction between the enolate and the non-enolizable compound can subsequently be effected.

* * * * *